United States Patent [19]

Gold et al.

[11] 4,284,555

[45] Aug. 18, 1981

[54] 7-CHLORO-8(SUBSTITUTED AMINO CARBONYLOXY)-1-PHENYL-2,3,4,5-TETRAHYDRO-1H-3-BENZAZEPINES

[75] Inventors: Elijah H. Gold, West Orange; Wei K. Chang, Livingston, both of N.J.

[73] Assignee: Schering Corporation, Kenilworth, N.J.

[21] Appl. No.: 34,055

[22] Filed: Apr. 27, 1979

[51] Int. Cl.³ .................. C07D 223/16; A61K 31/55
[52] U.S. Cl. ............................ 260/239 BB; 424/244
[58] Field of Search ................................ 260/239 BB

[56] References Cited

U.S. PATENT DOCUMENTS 3,609,138  9/1971  Mull et al. .................... 260/239 BB

FOREIGN PATENT DOCUMENTS 500194  1/1971  Switzerland ..................... 260/239 BB Primary Examiner—Donald G. Daus
Assistant Examiner—D. B. Springer
Attorney, Agent, or Firm—Carver C. Joyner

[57] ABSTRACT

This invention relates to substituted 1-phenyl-2,3,4,5-tetrahydro-1H-3-benzazepines. The compounds of this invention show neuroleptic, antidepressive and antiagressive activity.

6 Claims, No Drawings

7-CHLORO-8(SUBSTITUTED AMINO CARBONYLOXY)-1-PHENYL-2,3,4,5-TETRAHYDRO-1H-3-BENZAZEPINES

PRIOR ART

Substituted-1-phenyl-2,3,4,5-tetrahydro-1H-3-benzazepines have been previously described in the art, as for example, in U.S. Pat. No. 3,393,192, British Pat. No. 1,118,688, Danish Patent No. 123033, U.S. Pat. No. 3,609,138 and U.S. Pat. No. 4,011,319. The prior art has recognized that substituted-1-phenyl-2,3,4,5-tetrahydro-1H-3-benzazepines exhibit anti-bacterial effects, central nervous system effects and a hypotensive effect.

THE INVENTION

The novel compounds of this invention are the substituted 1-phenyl-2,3,4,5-tetrahydro-1H-3-benzazepines of the general formula I

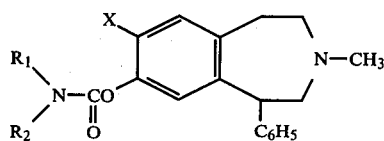

wherein
X is fluoro, chloro, bromo, trifluoromethyl or methyl;
$R_1$ is hydrogen, alkyl, aralkyl, cycloalkyl, aryl, hydroxyalkyl, alkoxyalkyl, or aminoalkyl of the formula

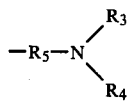

II, wherein
$R_5$ is alkyl,
$R_3$ is hydrogen or alkyl, and
$R_4$ is alkyl, or
the N-atom together with $R_3$ and $R_4$ is azetidinyl, pyrrolidinyl, piperidino, N-alkylpiperazinyl, morpholino or hexahydroazepinyl; and
$R_2$ is hydrogen provided that $R_1$ is not hydrogen, or alkyl, aralkyl, hydroxyalkyl or alkoxyalkyl; or the N-atom together with $R_1$ and $R_2$ is azetidinyl, pyrrolidinyl, piperidino, morpholino, N-alkylpiperazinyl, N-alkoxyalkylpiperazinyl, N-hydroxyalkylpiperazinyl, 3-hydroxyazetidinyl, 3-alkoxyazetidinyl, 3-hydroxypyrrolidinyl, 3-alkoxypyrrolidinyl, 3- or 4-hydroxypiperidino, 3- or 4-alkoxypiperidino, 4-oxopiperidino or 3-oxopyrrolidinyl;
wherein the alkyl and alkoxy groups contain 1 to 6 carbon atoms and the cycloalkyl groups 4 to 8 carbon atoms; and the pharmaceutically acceptable acid addition salts thereof.

The alkyl groups referred to above are exemplified by methyl, ethyl, propyl, butyl, pentyl, hexyl and the corresponding branched chain isomers thereof. The alkoxy groups are exemplified by methoxy, ethoxy, propoxy, butoxy, pentyloxy, hexyloxy and the branched chain isomers thereof. Preferably these groups contain 1 to 3 carbon atoms. If contained as substituents of heterocyclic groups alkyl and alkoxy groups preferably contain one to three carbon atoms.

The aryl groups are groups such as for example phenyl, alkyl-substituted-phenyl such as tolyl and xylyl.

The acid addition salts of the compounds of formula I can be derived from a variety of inorganic and organic acids such as for example sulfuric, phosphoric, hydrochloric, hydrobromic, hydroiodic, methanesulfonic, sulfamic, citric, lactic, pyruvic, oxalic, maleic, stearic, succinic, tartaric, fumaric, cinnamic, aspartic, acetic, benzoic, salicylic, gluconic, ascorbic and related acids.

The substituted 1-phenyl-2,3,4,5-tetrahydro-1H-3-benzazepines of formula I defined above can be prepared according to known methods.

The compounds of formula I can be prepared by reacting a 7-X-8-hydroxy-1-phenyl-2,3,4,5-tetrahydro-1H-3-benzazepine wherein X is as defined in the compound of formula I or a reactive derivative of the said benzazepine with a mono- or disubstituted amine

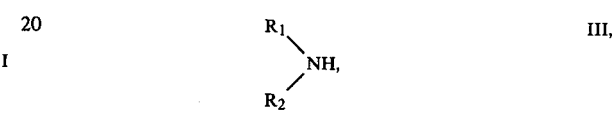

wherein $R_1$ and $R_2$ are as defined above for formula I or a reactive derivative of the said amine, whereby at least one of the reactants is in the form of a reactive derivative and one of the reactants provides the carbonyl group contained in the compound of formula I between the $R_1R_2N$-group and the oxygen at position 8.

For the preparation of a compound of the formula I wherein either $R_1$ or $R_2$ is hydrogen, the reactive derivative of the amine of formula III can be an isocyanate ($R_1NCO$ or $R_2NCO$), which is reacted with the appropriate 7X-8-hydroxy-1-phenyl-2,3,4,5-tetrahydro-1H-3-benzazepine. The reaction can be carried out in a polar non-hydroxylic solvent, such as for example acetonitrile. The reaction can be carried out at a temperature between zero° C. and 100° C., preferably at reflux temperature of the reaction mixture.

For the preparation of a compound of formula I containing a mono- or disubstituted carbamoyl group the above said process can be outlined by the following reaction scheme

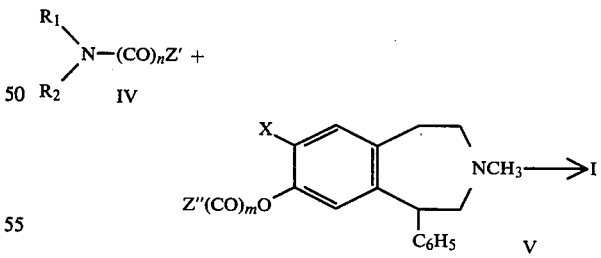

wherein $R_1$, $R_2$ and X are as defined above for formula I, one of n and m is one and the other is zero and Z' and Z" are eliminable groups.

According to this process an appropriate carbamoyl chloride, IV, in an anhydrous aprotic solvent can be reacted with an appropriate 7-X-8-hydroxy-1-phenyl-2,3,4,5-tetrahydro-1H-3-benzazepine, V. Preferably a suspension of the benzazepine in the solvent (e.g. anhydrous dimethoxy ethane), is first reacted with sodium hydride (e.g. 50% in mineral oil) until the evolution of gas ceases and then the carbamoyl chloride is added.

Alternatively, according to this process an appropriate amine; IV, wherein n is zero and Z' is hydrogen, can be reacted with an appropriate benzazepine V, wherein m is one and Z" is an eliminable group such as for example 1-imidazolyl or chloro.

The starting materials used in the above process can be prepared according to known methods.

In particular the carbonyl imidazolide and carbonyl chloride of the benzazepine, V, can be prepared from the appropriate 7-X-8-hydroxy-1-phenyl-2,3,4,5-tetrahydro-1H-3-benzazepine by reaction with N,N'-carbonyl diimidazole or phosgene. Typical reaction times are 0.5–48 hours and typical temperatures are the room temperatures to the reflux temperature of the particular reaction mixture.

The 7-X-8-hydroxy-1-phenyl-2,3,4,5-tetrahydro-1H-3-benzazepines starting materials mentioned above, many of which are novel compounds, can be prepared according to known methods. The 7-X-8-hydroxy-1-phenyl-2,3,4,5-tetrahydro-1H-3-benzazepines mentioned above as starting materials can be prepared for example by dealkylation of the corresponding 8-alkoxy compounds of the general formula VI

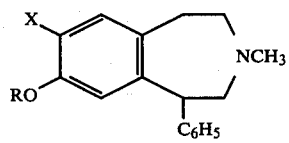

wherein R is alkyl and X is as defined for formula I. R is usually methyl but may also be any alkyl group e.g. containing up to 5 carbon atoms.

To cleave the alkoxy group and provide the hydroxy group at position 8, the compound of formula VI may be reacted with a strong acid, such as for example aqueous hydrogen halide, preferably hydrogen bromide, or sulfuric acid. The reaction can advantageously be performed under a nitrogen atmosphere. The reaction is usually carried out in an aqueous medium (e.g. using 48 percent aqueous hydrobromic acid) at about 75° to 100° C., preferably at reflux temperature of the reaction mixture, for about 2 to 24 hours.

Other typical dealkylating procedures are the use of sodium ethanethiolate in an aprotic solvent such as dimethylformamide at 100°–120° C. for 4–6 hours, or the use of pyridine hydrochloride at 200°–240° C. for 1–2 hours. Compound VI may be prepared by cyclization of a compound of the general formula VII

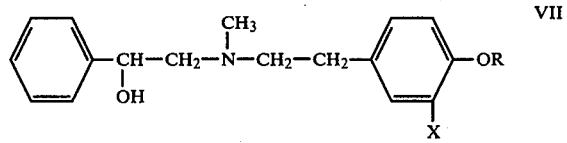

wherein X and R are as defined for formula VI. The compound of formula VII can be cyclized utilizing a dehydrating agent such as for example polyphosphoric acid, sulfuric acid, methane sulfonic acid, methane sulfonic acid/P$_2$O$_5$, zinc chloride and hydrogen fluoride. Especially preferred are sulfuric acid, methane sulfonic acid, methane sulfonic acid/P$_2$O$_5$, and hydrogen fluoride maintained at about −10° to 20° C.

A convenient way for preparing a compound of the general formula VII comprises the reaction of a 2-phenylethylamine with epoxyethylbenzene.

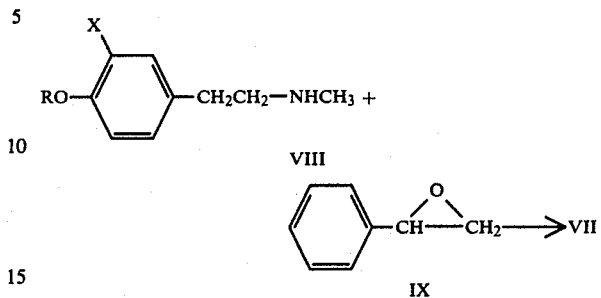

in a polar aprotic solvent such as acetonitrile, pyridine, dimethylformamide or dimethyl sulfoxide. The temperature at which the reaction is conducted is not critical, with room temperature to reflux being preferred.

Compound VI can also be prepared by introduction of the desired 7-substituent into an 8-alkoxy-1-phenyl-2,3,4,5-tetrahydro-1H-3-benzazepine containing no substituent or a replaceable substituent in position 7.

Compound VII can also be prepared by N-methylation of a corresponding 8-alkoxy-1-phenyl-2,3,4,5-tetrahydro-1H-3-benzazepine

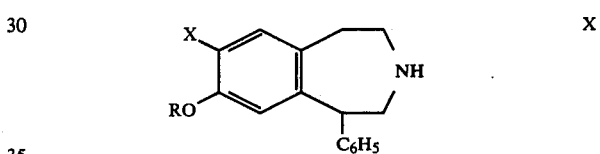

wherein R and X are as defined before. This N-methylation is accomplished in a conventional manner, a particularly facilitative method being the condensation of the compound of formula X with formaldehyde and formic acid. Alternatively, methyl chloride or methyl bromide may be used to methylate the compound. The compound of formula X can be prepared by known methods, for example analogously to the methods described above for the preparation of compound VI.

The compounds of formula I, as well as of formulae VI and X and of the 8-hydroxy analog of the compound of formula VI contain an asymmetric carbon atom in position 1 (chiral center). By the above described processes racemic mixtures of the relevant (R)- and (S)-isomers are obtained. Separation of the isomers can be effected by the usual well known techniques. If an (R)- or (S)- isomer of the compound of formula VI, its 8-hydroxy analog, or X is used as starting material in the preparation of the desired compound I, the corresponding isomer of the compound I is obtained by the process described above.

The (R)- and (S)- isomers of the said compounds can be resolved by techniques such as for example resolution by means of forming an adduct (e.g. of urea), chromatography, crystallisation from optically active solvents, resolution via diastereoisomeric salts (e.g. by means of N-acetyl-D-leucine), resolution by enzymatic processes (including destruction and chemical transformation of one isomer) and destruction of one isomer. It is preferred to use fractional crystallization.

The compounds of formula I can be transformed into pharmaceutically acceptable acid addition salts by reaction with a pharmaceutically acceptable acid or a reactive derivative thereof. Correspondingly the free compounds of formula I can be set free from the salts.

The compounds of this invention are typically formulated into conventional pharmaceutical compositions according to accepted procedures. The dosage of these compounds is dependent upon various factors, such as the particular compound employed and the patient's individual response. Preferably, the compositions will contain the active ingredient in an active but non-toxic amount selected from about 0.8 mg to about 200 mg of active ingredient per dosage unit.

The pharmaceutical carrier employed in the formulation of such compositions may be a solid or liquid. Typical carriers include, but are not limited to: sugars such as lactose, sucrose, mannitol and sorbitol; starches such as tapioca starch and potato starch; cellulose derivatives such as sodium carboxymethylcellulose, ethyl cellulose and methyl cellulose, gelatin; calcium phosphates such as dicalcium phosphate and tricalcium phosphate; sodium sulfate; calcium sulfate, polyvinyl alcohols; stearic acid; alkaline earth metal stearates such as calcium stearate; stearic acid vegetable oils such as peanut oil, cottonseed oil, sesame oil, olive oil and corn oil; non-ionic, cationic and anionic surfactants; ethylene glycol polymers, β-cyclodextrin; fatty alcohols and hydrolyzed cereal solids; as well as other non-toxic compatible fillers, binders, disintegrants and lubricants commonly used in pharmaceutical formulation. For injectable solutions sterile water and other steril ingredients have to be used.

Antipsychotic drugs are widely used e.g. in the treatment of schizophrenia. Their use is generally limited by their propensity to cause neurologic, autonomic and/or endocrine side effects. The compounds of this invention are novel antipsychotic drugs. The compounds have effects common to standard antipsychotic drugs but may be regarded as having a more generally better biological profile. Representative compounds of the invention have been found to have specific antipsychotic, antiaggression and anti-depressant activity with low potential for producing extrapyramidal, autonomic and hormonal side effects; the compounds did not show sedative and anti-convulsant activity. On this basis the compounds of this invention are useful agents for the treatment of manifestations of psychotic disorders due to their combination of neuroleptic, antidepressant and antiaggressive properties. The compounds are thus indicated for reducing excitement, hypermotility, abnormal initiative, affective tension and agitation through their inhabitory effects on psychomotor functions of the treated subjects. In particular these compounds are indicated as useful in the treatment of schizophrenia, mental depression, anxiety and hyperactive agitated behavioral states, particularly in mentally retarded patients.

The compounds of the invention may be co-administered intravenously with a narcotic to produce neuroleptic analgesia. Such a state provides sufficient CNS action to permit certain procedures (e.g. bronchoscopy x-ray studies, burn dressing, cystoscopy) to be performed without additional medication. Addition of inhaled nitrous oxide to the neuroleptic-narcotic combination would provide analgesia sufficient for surgical operations.

The daily dosage of the active ingredient is dependent upon various factors, such as the particular compound employed, the condition for which the compound is administered and the patient's individual response. Typical dosages for use as a neuroleptic, antidepressant or anti-aggressive agent, especially in the treatment of schizophrenia, mental depression, anxiety and hyperactive agitated behavioral states, particularly in mentally retarded patients, would vary from about 0.1 to 15, preferably 0.5 to 10 mg/kg per day divided in 3 or 4 doses, administered orally or parenterally.

The neuroleptic, antidepressant and antiaggressive properties of the compounds of this invention may be ascertained by testing in standardized assays such as are described in Barnett, et.al., Psychopharmacologia (Berl.) 36, 281–290 (1974).

The properties of the compounds of this invention can be illustrated by the following test results: (S)-7-chloro-8-dimethylaminocarbonyloxy-3-methyl-1-phenyl-2,3,4,5-tetrahydro-1H-3-benzazepine has an $ED_{50}$ of 5.7 mg/kg in the anti-muricide assay and an $ED_{50}$ of 1.2 mg/kg in the metamphetamine reversal assay. For this compound the $LD_{50}$ (oral dose in mice) is greater than 300 mg/kg.

Of the compounds defined by formula I above and its acid addition salts, those compounds are preferred wherein $R_1$ is hydrogen, alkyl, aralkyl, cycloalkyl, aryl, hydroxyalkyl, alkoxyalkyl, or aminoalkyl of the formula

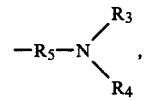

II, wherein $R_5$ is alkyl, $R_3$ is hydrogen or alkyl, and $R_4$ is alkyl; and $R_2$ is hydrogen provided that $R_1$ is not hydrogen, or alkyl, aralkyl, hydroxyalkyl or alkoxyalkyl; or the N-atom together with $R_1$ and $R_2$ is azetidinyl, pyrrolidinyl, piperidino, morpholino, 3-hydroxyazetidinyl, 3-alkoxyazetidinyl, 3-hydroxypyrrolidinyl, or 3-alkoxypyrrolidinyl;

especially those wherein X is chloro;

$R_1$ is hydrogen, methyl, ethyl, benzyl, phenyl, hydroxy- or methoxyalkyl, the alkyl group containing up to 3 carbon atoms, or dimethylaminoethyl;

$R_2$ is hydrogen provided $R_1$ is not hydrogen, methyl or ethyl; or the N-atom together with $R_1$ and $R_2$ is pyrrolidinyl, piperidino, morpholino, 3-hydroxyazetidinyl or 3-hydroxypyrrolidinyl.

In particular compounds are preferred which have the (S)-stereochemical configuration at position 1. Among these compounds are:

(S)-7-chloro-8-ethylaminocarbonyloxy-3-methyl-1-phenyl-2,3,4,5-tetrahydro-1H-3-benzazepine, (m.p. 133°–134.5° C.), (S)-7-chloro-8-(2-hydroxyethyl-methyl)aminocarbonyloxy-3-methyl-1-phenyl-2,3,4,5-tetrahydro-1H-3-benzazepine, (m.p. 236°–238° C.),*

(S)-7-chloro-8-(N-ethyl-N-methylamino)carbonyloxy-3-methyl-1-phenyl-2,3,4,5-tetrahydro-1H-3-benzazepine, (m.p. 276°–278° C.),*

(S)-7-chloro-8-(N-2-dimethylaminoethyl-N-methyl)aminocarbonyloxy-3-methyl-1-phenyl-2,3,4,5-tetrahydro-1H-3-benzazepine, (m.p. 183°–184° C.),**

(S)-7-chloro-8-(2-methoxyethyl)aminocarbonyloxy-3-methyl-1-phenyl-2,3,4,5-tetrahydro-1H-3-benzazepine, (m.p. 193°-195° C.),*

(S)-7-chloro-8-(3-hydroxy-1-azetidinyl)carbonyloxy-3-methyl-1-phenyl-2,3,4,5-tetrahydro-1H-3-benzazepine, (m.p. 241°-242° C.),*

(S)-7-chloro-8-dimethylaminocarbonyloxy-3-methyl-1-phenyl-2,3,4,5-tetrahydro-1H-3-benzazepine (m.p. 261°-263° C.),* and the pharmaceutically acceptable acid addition salts thereof. (The above melting points relate to the hydrochlorides, when marked by (*), and the dihydrochloride monohydrate, whem marked by (**), respectively).

The following Examples illustrate the preparation of the novel compounds of this invention.

EXAMPLE 1

(S)-7-chloro-8-(N-ethylaminocarbonyloxy)-3-methyl-1-phenyl-b 2,3,4,5-tetrahydro-1H-3-benzazepine A. Reflux for 16 hours, a solution of 21.0 g (0.113 moles) of 2-(3-chloro-4-methoxyphenyl)ethylamine and 13.6 g (0.113 moles) of epoxyethylbenzene in 75 ml of acetonitrile. Remove the solvent and triturate the residue with 30 ml of ether. Filter and digest the precipitate twice with 60 ml of isopropyl ether and obtain N-[2-(3-chloro-4-methoxyphenyl)ethyl]-2-phenyl-2-hydroxyethylamine, m.p. 95°-96° C.

B. Add in small portions, 12.0 g (0.0394 moles) of the product of step A to 60 ml of concentrated sulfuric acid with cooling (ice bath) and stirring so that the temperature of the reaction mixture stays at 10°±5° C. Stir at 10° C. for 30 minutes, then for another hour at 25° C. Pour onto 500 g of ice, and then carefully add 100 ml of concentrated ammonium hydroxide, following this with the careful addition of 30 g of solid sodium hydroxide with cooling in an ice-bath, not allowing the temperature to rise above 30° C. Extract with 300 ml of benzene. Separate the benzene layer and dry over anhydrous sodium sulfate. Remove the solvent to obtain (R,S)-7-chloro-8-methoxy-1-phenyl-2,3,4,5-tetrahydro-1H-3-benzazepine as a pale yellow syrup. Prepare the acid maleate in ethanol and recrystallize this crude salt from ethanol to obtain an analytically pure sample, m.p. 171°-173° C.

C. Heat to reflux to dissolve a mixture of 9.60 g (0.033 moles) of the product of step B and 5.80 g (0.033 moles) of N-acetyl-D-leucine in 180 ml of acetonitrile. Cool slowly to room temperature. Filter and recrystallize the salt repeatedly from acetonitrile to obtain (S)-7-chloro-8-methoxy-1-phenyl-2,3,4,5-tetrahydro-1H-3-benzazepine N-acetyl-D-leucinate, m.p. 171°-173° C. $[\alpha]_D^{26} = +27.7°$ (c=1, ethanol). Stir 1 g of this salt in a mixture of 20 ml of 0.5 N sodium hydroxide and 20 ml of ether to total dissolution. Separate the ether layer, dry over anhydrous sodium sulfate, and evaporate to obtain (S)-7-chloro-8-methoxy-1-phenyl-2,3,4,5-tetrahydro-1H-3-benzazepine as a colorless solid. Recrystallize from ethyl ether to obtain an analytically pure sample, m.p. 81°-82° C. $[\alpha]_D^{26} = +38.3°$ (c=1, ethanol).

D. Reflux for 4 hours, a solution of 52.0 g (0.18 moles) of the product of step C in a mixture of 96 ml of 37% formaldehyde and 144 ml of 90% formic acid. Distill almost to dryness at 100° C. under reduced pressure (about 100 mm). Dissolve the residue in a mixture of 500 ml of 1 N sodium hydroxide and 500 ml of ethyl ether with cooling and stirring. Separate the ether layer, dry over anhydrous sodium sulfate, and evaporate to give (S)-7-chloro-8-methoxy-3-methyl-1-phenyl-2,3,4,5-tetrahydro-1H-3-benzazepine as a colorless solid. Obtain an analytically pure sample by crystallization from ethyl ether, m.p. 91°-92° C. $[\alpha]_D^{26} = +47.3°$ (c=1, ethanol).

E. Heat and stir a mixture of 0.850 g (0.0028 moles) of the product of step D in 12 ml of 48% hydrobromic acid at 100° C. for 16 hours. Dilute with 75 ml of water and heat on a steam bath to dissolve. Adjust to about pH 8 with solid sodium bicarbonate, filter, and wash the resulting precipitate with water. Recrystallize from ethanol to obtain analytically pure (S)-7-chloro-8-hydroxy-3-methyl-1-phenyl-2,3,4,5-tetrahydro-1H-3-benzazepine, m.p. 188°-189° C. $[\alpha]_D^{26} = +44.8°$ (c=1, dimethylformamide).

F. Dissolve 1.22 g (0.0042 moles) of the product of step E in 60 ml of refluxing acetonitrile and add dropwise 0.6 ml of ethyl isocyanate with stirring. Reflux for 30 minutes after addition is complete. Evaporate to dryness and crystallize the residue from acetonitrile to obtain analytically pure (S)-7-chloro-8-(ethylaminocarbonyloxy)-3-methyl-1-phenyl-2,3,4,5-tetrahydro-1H-3-benzazepine, m.p. 133°-134.5° C. $[\alpha]_D^{26} = +20.2°$ (c=0.5, ethanol).

EXAMPLE 2

(S)-7-chloro-8-dimethylaminocarbonyloxy-3-methyl-1-phenyl-2,3,4,5-tetrahydro-1H-3-benzazepine hydrochloride Add in small portions with stirring, 360 mg of sodium hydride (50% in mineral oil) to a suspension of 2.16 g (0.0075 moles) of (S)-7-chloro-8-hydroxy-3-methyl-1-phenyl-2,3,4,5-tetrahydro-1H-3-benzazepine (as obtained in step E of Example 1) in 35 ml of anhydrous dimethoxyethane and stir until the evolution of gas ceases. Add dropwise a solution of 0.75 ml of dimethylcarbamyl chloride in 5 ml of anhydrous dimethoxyethane. Stir for 36 hours at room temperature and concentrate to dryness; dissolve the residue in 50 ml of ethyl ether and filter to remove the solid. Wash the filtrate twice with 30 ml of 0.5 N sodium hydroxide, dry the ether layer over anhydrous sodium sulfate, and precipitate (S)-7-chloro-8-dimethylaminocarbonyloxy-3-methyl-1-phenyl-2,3,4,5-tetrahydro-1H-3-benzazepine hydrochloride with 1 N ethereal hydrogen chloride. Obtain an analytical sample by crystallization from 2-propanol, m.p. 261°-263° C. $[\alpha]_D^{26} = +23.1°$ (c=1, dimethylformamide).

EXAMPLE 3

(S)-7-bromo-8-dimethylaminocarbonyloxy-3-methyl-1-phenyl-2,3,4,5-tetrahydro-1H-3-benzazepine hydrochloride A. Hydrogenate a solution of 21.10 g (0.07 moles) of (S)-7-chloro-8-methoxy-3-methyl-1-phenyl-2,3,4,5-tetrahydro-1-H-3-benzazepine (e.g. obtained as described in Example 1, step D) 3.30 g (0.0825 moles) of sodium hydroxide in 300 ml of 95% ethanol at room temperature and at 4.2 kg/cm$^2$ (=60 psi), with 1.70 g of 20% palladium hydroxide-on-carbon until the theoretical amount of hydrogen is consumed. Remove the catalyst and concentrate the filtrate to dryness on a steam bath at about 100 mm. Stir the residue with a mixture of 100 ml of water and 150 ml of ethyl ether to total dissolution. Separate the ether layer, dry over anhydrous sodium sulfate, and evaporate to dryness. Crystallize the residue from hexane to obtain analytically pure (S)-8- methoxy-3-methyl-1-phenyl-2,3,4,5-tetrahydro-1H-3-benzazepine, m.p. 50°–51° C., $[\alpha]_D^{26} = +51.8°$ (c=1, ethanol).

B. Warm a solution of 6.17 g (0.023 moles) of the product of Step A in 46 ml of glacial acetic acid (containing 3.0 g of anhydrous hydrobromic acid) and add dropwise a solution of 33.5 ml of bromine in glacial acetic acid (0.186 g/ml) with stirring. Stir at room temperature for 2.5 hours after the addition is complete and then for 5 minutes at 100° C. Pour the reaction mixture into 600 ml of ice, basify with excess 50% sodium hydroxide, and extract with 200 ml of ethyl ether. Separate the ether layer and dry over anhydrous sodium sulfate. Precipitate (S)-7-bromo-8-methoxy-3-methyl-1-phenyl-2,3,4,5-tetrahydro-1H-3-benzazepine hydrochloride with 1 N ethereal hydrogen chloride as a gummy solid. Crystallize from ethanol, to obtain a colorless solid, m.p. 263°–265° C.

C. Heat for 16 hours at 115° C. a mixture of 2.04 g (0.0059 moles) of the product of step B in 20 ml of 48% hydrobromic acid. Pour the reaction mixture into 180 ml of boiling water and adjust the pH to about 8 with solid sodium bicarbonate. Cool to room temperature and extract with 150 ml chloroform. Separate the chloroform layer, dry over anhydrous sodium sulfate, and evaporate to give a viscous gum. Purify through a silica gel column (50 g thin layer chromatography grade), with chloroform:ethanol:ammonium hydroxide (90:2:0.5) as eluent, to obtain (S)-7-bromo-8-hydroxy-3-methyl-1-phenyl-2,3,4,5-tetrahydro-1H-3-benzazepine as a colorless syrup. Prepare the acid maleate and crystallize from ethanol, m.p. 197°–199° C., $[\alpha]_D^{26} = -0.7°$ (c=1, dimethylformamide).

D. Add in small portions with stirring, 360 mg of sodium hydride (50% in mineral oil) to a suspension of 2.42 g (0.0075 moles) of the product of step C in 35 ml of anhydrous dimethoxyethane and stir until the evolution of gas ceases. Add dropwise a solution of 0.75 ml of dimethylcarbamyl chloride in 5 ml of anhydrous dimethoxyethane. Stir for 36 hours at room temperature and concentrate to dryness; dissolve the residue in 50 ml of ethyl ether and filter to remove the solid. Wash the filtrate twice with 30 ml of 0.5 N sodium hydroxide, dry the ether layer over anhydrous sodium sulfate, and precipitate (S)-7-bromo-8-dimethylaminocarbonyloxy-3-methyl-1-phenyl-2,3,4,5-tetrahydro-1H-3-benzazepine hydrochloride with 1 N ethereal hydrogen chloride.

In a manner analog to those described above also other compounds of this invention, in free form or in the form of their salts, can be prepared, such as for example:

(S)-7-chloro-8-diethylaminocarbonyloxy-3-methyl-1-phenyl-2,3,4,5-tetrahydro-1H-3-benzazepine, (m.p. 281°–283° C.),*

(S)-7-chloro-3-methyl-1-phenyl-8(1-piperidylcarbonyloxy)-2,3,4,5-tetrahydro-1H-3-benzazepine, (m.p. 282°–284° C.),*

(S)-7-chloro-3-methyl-8-(N-methyl-N-phenylamino)carbonyloxy-1-phenyl-2,3,4,5-tetrahydro-1H-3-benzazepine, (m.p. 242°–244° C.),*

(S)-7-chloro-3-methyl-8-(morpholinocarbonyloxy)-1-phenyl-2,3,4,5-tetrahydro-1H-3-benzazepine, (m.p. 287°–289° C.),*

(S)-8-(N-benzyl-N-methyl)aminocarbonyloxy-7-chloro-3-methyl-1-phenyl-2,3,4,5-tetrahydro-1H-3-benzazepine, (m.p. 216°–218° C.),*

(S)-7-chloro-3-methyl-1-phenyl-8-(1-pyrrolidylcarbonyloxy)-2,3,4,5-tetrahydro-1H-3-benzazepine, (m.p. 276°–278° C.),*

(S)-7-chloro-3-methyl-8-methylaminocarbonyloxy-1-phenyl-2,3,4,5-tetrahydro-1H-3-benzazepine, (m.p. 143°–144.5° C.), (S)-7-chloro-8-(2-hydroxyethyl-methyl)aminocarbonyloxy-3-methyl-1-phenyl-2,3,4,5-tetrahydro-1H-3-benzazepine, (m.p. 236°–238° C.),*

(S)-8-benzylaminocarbonyloxy-7-chloro-3-methyl-1-phenyl-2,3,4,5-tetrahydro-1H-3-benzazepine, (m.p. 171°–173° C.),*

(S)-7-chloro-8-(N-ethyl-N-methylamino)carbonyloxy-3-methyl-1-phenyl-2,3,4,5-tetrahydro-1H-3-benzazepine, (m.p. 276°–278° C.),*

(S)-7-chloro-8-(N-2-dimethylaminoethyl-N-methyl)-aminocarbonyloxy-3-methyl-1-phenyl-2,3,4,5-tetrahydro-1H-3-benzazepine, (m.p. 183°–184° C.),**

(S)-7-chloro-8-(2-methoxyethyl)aminocarbonyloxy-3-methyl-1-phenyl-2,3,4,5-tetrahydro-1H-3-benzazepine, (m.p. 193°–195° C.),*

(S)-7-chloro-8-(3-hydroxy-1-azetidinyl)carbonyloxy-3-methyl-1-phenyl-2,3,4,5-tetrahydro-1H-3-benzazepine, (m.p. 241°–242° C.),*

(S)-7-chloro-8-(3-hydroxy-1-pyrrolidinyl)carbonyloxy-3-methyl-1-phenyl-2,3,4,5-tetrahydro-1H-3-benzazepine, (m.p. 110°–150° C.),***

(S)-7-chloro-8-(2-hydroxyethyl)aminocarbonyloxy-3-methyl-1-phenyl-2,3,4,5-tetrahydro-1H-3-benzazepine, (m.p. 126°–127° C.), (S)-7-chloro-8-(N-methyl-N-3-hydroxypropyl)aminocarbonyloxy-3-methyl-1-phenyl-2,3,4,5-tetrahydro-1H-3-benzazepine, (S)-7-chloro-8-(N-methyl-N-2-methoxyethyl)aminocarbonyloxy-3-methyl-1-phenyl-2,3,4,5-tetrahydro-1H-3-benzazepine, (S)-3,7-dimethyl-8-dimethylaminocarbonyloxy-1-phenyl-2,3,4,5-tetrahydro-1H-3-benzazepine, and corresponding 7-fluoro, 7-bromo, 7-methyl and 7-trifluoromethyl compounds.

(Most of the above melting points relate to salts of the named compounds: to the hydrochloride where marked by (*), to the dihydrochloride monohydrate where marked by () and to the hydrochloride monohydrate where marked by (*).

The following formulations illustrate some of the dosage forms in which the compounds of this invention may be employed (Compound A mentioned in the formulation examples is (S)-7-chloro-8-dimethylaminocarbonyloxy-3-methyl-1-phenyl-2,3,4,5-tetrahydro-1H-3-benzazepine hydrochloride).

| Formulation 1 Enteric Coated Tablets | mg/core |
|---|---|
| Compound A | 100.0 |
| Citric Acid | 1.0 |
| Lactose, USP | 33.5 |
| Dicalcium Phosphate | 70.0 |
| Nonionic Surfactant (*Pluronic F-68) | 30.0 |
| Sodium Lauryl Sulfate | 15.0 |
| Polyvinylpyrrolidine | 15.0 |
| Polyethylene Glycol (*Carbowax 1500) | 4.5 |
| Polyethylene Glycol (Carbowax 6000) | 45.0 |
| Denatured Alcohol 50 ml/1000 cores | |
| Corn Starch | 30.0 |
| Dry | |
| Sodium Lauryl Sulfate | 3.0 |
| Magnesium Stearate | 3.0 |

-continued

| Formulation 1 Enteric Coated Tablets | mg/core |
|---|---|
| Tablet Weight | 350.0 |

[*Pluronic and Carbowax are Registered Trade Marks]

Procedure

Compound A is mixed with the citric acid, lactose, dicalcium phosphate, the pluronic and sodium lauryl sulfate. The above mixture is screened through a No. 60 screen and damp granulated with an alcoholic solution consisting of polyvinylpyrrolidone, carbowax 1500 and 6000. Add additional alcohol, if necessary, to bring powders to a pasty mass. Add corn starch and continue mixing until uniform granules are formed. Pass through a No. 10 screen, tray and dry in an oven at 100° C. for 12-14 hours. Reduce dried granulation through a No. 16 screen, add sodium lauryl sulfate and magnesium stearate, mix and compress into desired shape on a tablet machine.

Coating

The above cores are treated with a lacquer and dusted with talc to prevent moisture adsorption. Sub-coat layers are added to round out the core. A sufficient number of lacquer coats are applied to make the core enteric. Additional sub-coats and smoothing coats are applied to completely round out and smooth the tablet. Color coats are applied until desired shade is obtained. After drying the coated tablets are polished to give the tablets an even gloss.

| Formulation 2 Capsules | mg/capsule |
|---|---|
| Compound A | 100.00 |
| Citric Acid | 1.00 |
| Nonionic Surfactant (Pluronic, F-68) | 40.00 |
| Sodium Lauryl Sulfate | 20.00 |
| Lactose | 238.00 |
| Magnesium Stearate | 1.00 |
| | 400.00 |

Procedure

Mix together Compound A, citric acid, pluronic, sodium lauryl sulfate and lactose. Pass through a No. 80 screen. Add magnesium stearate, mix and encapsulate into two-piece gelatin capsules of an appropriate size.

| Formulation 3 Suppository | mg/2gms |
|---|---|
| Compound A | 100 |
| Theobroma Oil, Pharm. Grade to make | 2 gms |

Procedure

Prepare a slurry of the Compound A with a portion of the melted theobroma oil and pass the slurry through a suitable colloid mill until it is free of grittiness. Add sufficient melted theobroma oil to bring the batch to final weight. Pour the melted mix, while maintaining uniformity, into appropriately prepared molds and allow to cool.

Test Descriptions

Anti-muricide assay: Male Long Evans rats weighing 225-250 g are housed 1 rat per cage, and killers (rats show an instinctive mouse killing behavior (muricide)) are selected initially after being deprived of food for approximately 66 hours. This is the only time the rats are deprived of food. Food, ad libitum, is avaiable on the cage floor since food bins are not practical because they afford a hiding place for mice. The rats are tested for muricidal behavior the following day and once a week thereafter; non-killers are always eliminated. A non-killer is a rat which fails to kill a mouse placed into his cage within 5 minutes. Drugs are tested in the afternoon of the day following this weekly check for persistance of the killing behavior. Since the rats are not deprived of food or water and rarely attempt to eat the mouse, this behavior is not motivated by hunger. Four weeks after the first test for killing, the rats are injected, i.p., with placebo and then tested 30/60 minutes after the injection. Rats that do not kill are eliminated. Only rats that consistantly kill mice placed in their home cages are used for drug testing. Every treatment-group is comprised of 5 rats. Each rat is presented with a CFI male albino mouse at 30 and 60 minutes after the intraperitoneal injection (1 ml/kg) of test drug. Blockade of muricidal behavior is determined by observing the number of surviving mice 5 minutes after being introduced into the rat cages. The result is expressed in ED$_{50}$ values, which means that at the given dosage 50% of the tested rats do not kill mice.

Methamphetamine reversal assay: Groups of 10 mice are aggregated in a 11×26×13 cm plastic chamber. Test drugs are given orally thirty minutes prior to an intraperitoneal administration of methamphetamine at 15 mg/kg. (This dose of methamphetamine is about 1.5 times the LD$_{50}$ under these conditions and usually kills at least 90 percent of the animals). As a control perphenazine at 1 mg/kg is used. (this dose of perphenazine usually affords complete protection.) The number of deaths in each group are counted 4 hours later

We claim:

1. A compound of the formula

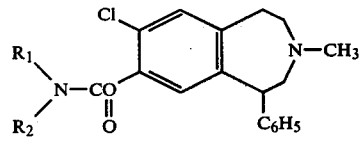

and the pharmaceutically acceptable acid addition salts thereof wherein $R_1$ and $R_2$ are members of the group consisting of hydrogen, alkyl, methoxyalkyl, and hydroxy alkyl wherein the alkyl and alkoxy groups have 1 to 6 carbon atoms.

2. A compound of claim 1 wherein $R_1$ is hydrogen and $R_2$ is ethyl, said compound being 7-chloro-8-ethylaminocarbonyloxy-3-methyl-1-phenyl-2,3,4,5-tetrahydro-1H-3-benzazepine.

3. A compound of claim 1 wherein $R_1$ is hydrogen and $R_2$ is 2-hydroxyethyl-methyl, said compound being 7-chloro-8-(2-hydroxyethyl-methyl)aminocarbonyloxy-3-methyl-1-phenyl-2,3,4,5-tetrahydro-1H-benzazepine.

4. A compound of claim 1 wherein $R_1$ is ethyl and $R_2$ is methyl, said compound being 7-chloro-8-(N-ethyl-N- methylamino)-carbonyloxy-3-methyl-1-phenyl-2,3,4,5-tetrahydro-1H-3-benzazepine.

5. A compound of claim 1 wherein $R_1$ is hydrogen and $R_2$ is 2-methoxyethyl, said compound being 7-chloro-8-(2-methoxyethyl)aminocarbonyloxy-3-methyl-1-phenyl-2,3,4,5-tetrahydro-1H-3-benzazepine.

6. A compound of claim 1 wherein $R_1$ and $R_2$ are methyl, said compound being 7-chloro-8-dimethylaminocarbonyloxy-3-methyl-1-phenyl-2,3,4,5-tetrahydro-1H-3-benzazepine.

* * * * *